(12) United States Patent
Pfeiffer

(10) Patent No.: US 6,642,388 B1
(45) Date of Patent: Nov. 4, 2003

(54) METHOD FOR PRODUCING 2-AMINOMETHYL-4-CYANO-THIAZOL

(75) Inventor: Thomas Pfeiffer, Boehl-lggelheim (DE)

(73) Assignee: Abbott GmbH & Co. KG, Munich (DE)

( * ) Notice: Subject to any disclaimer, the term of this patent is extended or adjusted under 35 U.S.C. 154(b) by 0 days.

(21) Appl. No.: 10/031,700

(22) PCT Filed: Jul. 11, 2000

(86) PCT No.: PCT/EP00/06562
§ 371 (c)(1),
(2), (4) Date: May 10, 2002

(87) PCT Pub. No.: WO01/07425
PCT Pub. Date: Feb. 1, 2001

(30) Foreign Application Priority Data

Jul. 23, 1999 (DE) .......................................... 199 23 861

(51) Int. Cl.[7] ............................................. C07D 277/04
(52) U.S. Cl. ........................................ 548/201; 548/202
(58) Field of Search ................................. 548/201, 202

(56) References Cited

U.S. PATENT DOCUMENTS 6,114,358 A     9/2000    Baucke et al. ............... 514/336

FOREIGN PATENT DOCUMENTS

| EP | 0 928 790 | 7/1999 |
| WO | WO 00/39124 | 7/2000 |
| WO | WO 0107426 A1 * | 2/2001 |

OTHER PUBLICATIONS

Videnov G. et al, 1996, "Synthesis of naturally occuring, conformationally restricted tripepetide mimetics."; Angewandte Chemie. International EDition, Verlag Chemie. Weinheim, DE, Bd. 35, Nr 13/14, p. 1503–1506.*
Schmidt et al. "Amino Acids and Peptides; 59[1] Synthesis of Biologically Active Cyclopeptides; 9[2] Synthesis of 16 Isomers of Dolastatin 3;[3] I. Synthesis of the 2–(1–aminoalkyl)–thiazole–4–carboxylic Acids" Synthesis No. 3 (1987) pp. 233–236.
Cross et al. "Peptides Part XIV[1] thiazoleamino–acids, Degradation Products of Thiostrepton Petides Part XIV" Jn. of Chem. Soc. (1963) pp. 2143–2150.
Lange et al. "A New Mild Method for the Synthesis of Amidines" Tetrahedron Letters No. 40 (1999) pp. 7067–7070.
Bernier et al. "Analog of Dolastatin 3 Synthesis, $^1$H NMR Studies and Spatial Conformation" Tetrahedron vol. 42 No. 10 (1986) pp. 2695–2702.

Videnov et al. "Synthesis of Naturally Occuring Conformationally Restricted Oxazole– and Thiazole–Containing Di– and Tripeptide Mimetics" Anges. Chem. Int. Ed. Engl. No. 13114 (1996) pp. 1503–1506.
Bailly et al. "Depsipeptide Analogs of th Antitumor Drug Distamycin Containing Thiazole Amino Acids Residues" Tetrahedron vol. 44 No. 18 (1988) pp. 5833–5843.

* cited by examiner

Primary Examiner—Joseph K. McKane
Assistant Examiner—Robert Shiao
(74) Attorney, Agent, or Firm—Wood, Phillips, Katz, Clark & Mortimer

(57) ABSTRACT

The invention relates to processes for preparing 2-aminomethyl-4-cyanothiazole and its salts of the formulae Ia and Ib

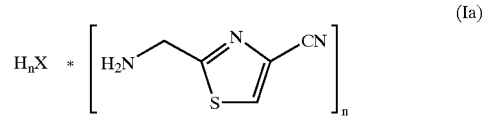

(Ia)

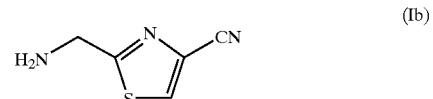

(Ib)

in which
n=1 or 2 and,
for n=1, X is chloride, bromide, triflate and hydrogen sulfate and
for n=2, X is sulfate, comprising the process step where the thioamide of the formula IV

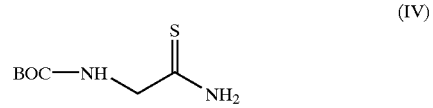

(IV)

is stirred with a bromopyruvate of the formula V,

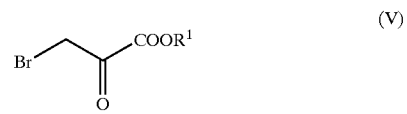

(V)

in which $R^1$ is branched or linear $C_{1-4}$-alkyl in an alcohol $R^2OH$ in which $R^2$ is branched or linear $C_{1-8}$-alkyl, $HO-CH_2-CH_2-$, $HO-CH_2-CH_2-CH_2-$ or $C_{1-4}$-alkyl-$O-CH_2-CH_2-$ at from $-5°$ C. to $40°$ C. until the conversion of the thioamide IV has essentially gone to completion, and to the compounds of the formulae Ia and Ib.

8 Claims, No Drawings

METHOD FOR PRODUCING 2-AMINOMETHYL-4-CYANO-THIAZOL

This application is a 371 of PCT/EP00/06562 Jul. 11, 2000.

The present invention relates to a novel process for preparing 2-aminomethyl-4-cyanothiazole.

The synthesis of 2-aminomethylthiazoles which contain a functional group such as a carboxylic acid, a carboxylic ester, a carboxamide or a carbothioamide in the 4-position has been described in the literature; literature (1): J.-L. Bernier, R. Houssin, J.-P. Henichart, Tetrahedron 42 (1986), 2695; literature (2): U. Schmidt et al., Synthesis (1987), 233; literature (3): G. Jung et al., Angew. Chem. Int. Ed. 35 (1996), 1503; literature (4): WO 9806741; literature (5): Kenner et al., J. Chem. Soc. (1963), 2143.

The abovementioned processes known from the literature have been described for small laboratory batches and are, for some reaction steps, not particularly suitable for a preparation on an industrial scale. For example, literature (2) describes the synthesis of the 4-ethoxycarbonylthiazole derivative using a Z protective group (Z=benzyloxycarbonyl). However, the Z protective group can, after conversion of the corresponding carboxamide into the Z-protected 2-aminomethyl4-cyanothiazole, no longer be removed by methods known from the literature (for example hydrogenolytically or with HBr) on an industrial scale with the cyano group remaining intact.

The 2-benzamidomethyl-4-ethoxycarbonylthiazole, which is described in literature (5), is, after further conversion into the corresponding benzoyl-protected 4-cyanothiazole, likewise unsuitable for removing the protective group with the cyano group remaining intact.

Literature (3) describes the synthesis of the 4-hydroxycarbonylthiazole derivative using the BOC protective group (BOC=tert-butyloxycarbonyl) which can be cleaved off with the cyano group remaining intact. However, a precursor of the thiazole derivative, i.e. the N-BOC-glycinethioamide, is synthesized from the BOC-glycinamide using Lawson's reagent which, when used on an industrial scale, would involve considerably higher costs than the hydrogen sulfide method described in literature (2). Lawson's reagent is also employed in literature (1).

The authors of literature (3) describe the cyclization to the 4-carboxylic acid of the thiazole using bromopyruvic acid. This route is also possible on an industrial scale; however, it has the disadvantage that bromopyruvic acid is less stable than ethyl bromopyruvate, which is used in literature (1), (2) and (5), and that the preparation of the thiazole carboxamide via the thiazole carboxylic acid involves higher technical expense. Moreover, it was not possible to achieve the thiazole carboxylic acid yield described in literature (3) on a larger scale when using $CaCO_3$.

Using the procedure described in literature (1), the preparation of ethyl thiazole carboxylate with ethyl bromopyruvate in diethyl ether was very much incomplete. Instead of the stated reaction time of 3 h, our own studies showed that even after 20 h only some of the starting material (thioamide) had reacted. The desired ethyl thiazole carboxylate had indeed been formed in addition to a number of byproducts; however, in none of the experiments was it possible to even come close to the stated yield.

Likewise, it was not possible to employ the procedure, described in literature (2), for the cyclization to the thiazole carboxylic ester successfully. The use of ethanol at 65° C. in the presence of molecular sieves resulted in rapid cleavage of the BOC protective group, owing to HBr being formed. Even at 40° C. in ethanol and with other alcohols (for example methanol or isopropanol), it was not possible to realize the procedure of literature (2) with yields >70%. Addition of basic solution did likewise not lead to higher yields.

2-Aminomethyl-4-cyanothiazole would be an interesting intermediate for preparing serine protease-inhibiting low-molecular-weight substances (for example thrombin inhibitors), if it was readily available industrially. Such thrombin inhibitors are mentioned, for example, in WO 9806741. 2-Aminomethy-4-cyanothiazole can also be employed for preparing other thrombin inhibitors and prodrugs thereof, for example N-(ethoxycarbonyl-methylene)-(D)-cyclohexylalanyl-3,4-dehydroprolyl-[2-(4-hydroxyamidino)-thiazole]methylamide hydrochloride.

It is an object of the present invention to provide a process for preparing 2-aminomethy-4-yanothiazole, thus making available this synthesis building block for further syntheses, in a cost-effective manner.

We have found that this object is achieved by cyclizing the thioamide with the bromopyruvate without addition of bases and without addition of molecular sieves in alcohol at room temperature with a yield of almost 90%. The yield depends highly on the dilution of the starting materials in alcohol and reaches its maximum after a reaction time of about 5 h. The reaction in alcoholic solution is preferably carried out in a concentration range of less than 0.75 mol/l, based on thioamide (IV). Particular preference is given to a concentration of from more than 0.25 mol/l to 0.55 mol/l, based on IV. At concentrations of 1 mol/l, the reaction no longer proceeds with satisfactory yields. According to the invention, the reaction temperature is in the range from −5° C. to 40° C., preferably in the range from 5° C. to 30° C. and in particular from 10° C. to 25° C. At 65° C., as in literature (2), little BOC-protected thiazole carboxylic ester, if any, can be isolated after less than 5 h, even at a relatively high dilution. In the series of the alcohols, it was possible to obtain higher yields with isopropanol than with methanol. Small amounts of water do not negatively affect the cyclization, so that dehydrating agents such as molecular sieves can advantageously be dispensed with.

Also unexpected was the aminolysis of the thiazole carboxylic ester with aqueous ammonia to give the thiazole carboxamide. Reaction was observed only on addition of substantially more than two molar equivalents $NH_3$. Preference is given to an excess of at least 5 molar equivalents $NH_3$, in particular to values of at least 10 molar equivalents $NH_3$. The solubilizer used can likewise be alcohol. However, in the series of the alcohols, yields with methanol were higher than with isopropanol.

Thiazole carboxylic ester can be obtained in crystalline form. To remove the solvent, it is necessary to scavenge the HBr formed using bases. Under pH control, it is possible to use dilute aqueous sodium hydroxide solution or else ammonia for this purpose. By hydrolyzing the ester with, for example, aqueous sodium hydroxide solution and subsequently adding acid in a pH-controlled manner, it is also possible to prepare the corresponding BOC-protected thiazole carboxylic acid in a simple manner and with good yields by this route.

For a synthesis on an industrial scale, it is advantageous to prepare the thiazole carboxamide without isolating the ester in a one-pot process. Starting with the thioamide, it is then possible to achieve a yield of >60% of crystalline amide with small technical expense.

The conversion into the 2-aminomethyl-4-cyanothiazole can then easily be effected by dehydration with, for example, trifluoroacetic anhydride and subsequent gentle removal of the BOC protective group.

The present invention relates to a process for preparing 2-aminomethyl-4-cyanothiazole and its salts of the formulae Ia and Ib,

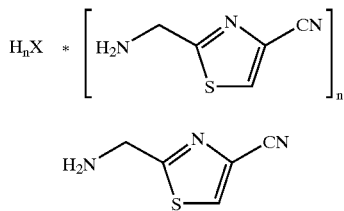

in which
  n=1 or 2 and,
  for n=1, X is chloride, bromide, triflate and hydrogen sulfate and,
  for n=2, X is sulfate,
which can be carried out by introducing the tert-butyloxycarbonyl protective group (BOC) at the nitrogen of the aminoacetonitrile, subsequently adding hydrogen sulfide to the nitrile group, cyclizing this N-BOC-glycinethioamide with bromopyruvate according to Scheme A to give the corresponding thiazole-4-carboxylic ester and then the thiazole-4-carboxamide and finally the 4-cyanothiazole derivative.

Shown in Scheme A, an advantageous process which can easily be carried out on an industrial scale is described:

The aminoacetonitrile II is commercially available as a salt (sulfate, hydrogen sulfate, chloride), or as a free base.

The intermediates III to VII are mentioned in the literature references (1) and (3) (V and VI in each case as the ethyl ester).

The 4-cyanothiazoles VIII and IX are novel.

According to this process, the intermediates III, VI and VII can be converted advantageously, without further work-up, into the respective subsequent product. The 4-cyanothiazole salt IX, which is embraced by the formula Ia, can be reacted under pH-controlled conditions with bases to give the salt-free form of the formula Ib.

The invention furthermore provides processes for preparing 2-aminomethyl-4-cyanothiazole and its salts of the formulae Ia and Ib

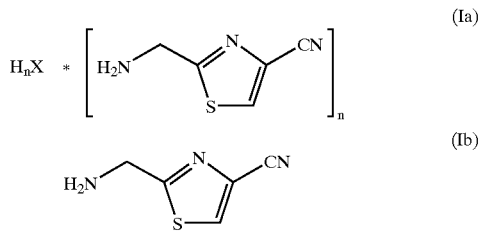

in which
  n=1 or 2 and,
  for n=1, X is chloride, bromide, triflate and hydrogen sulfate and,
  for n=2, X is sulfate. In the process according to the invention, the thioamide of the formula IV

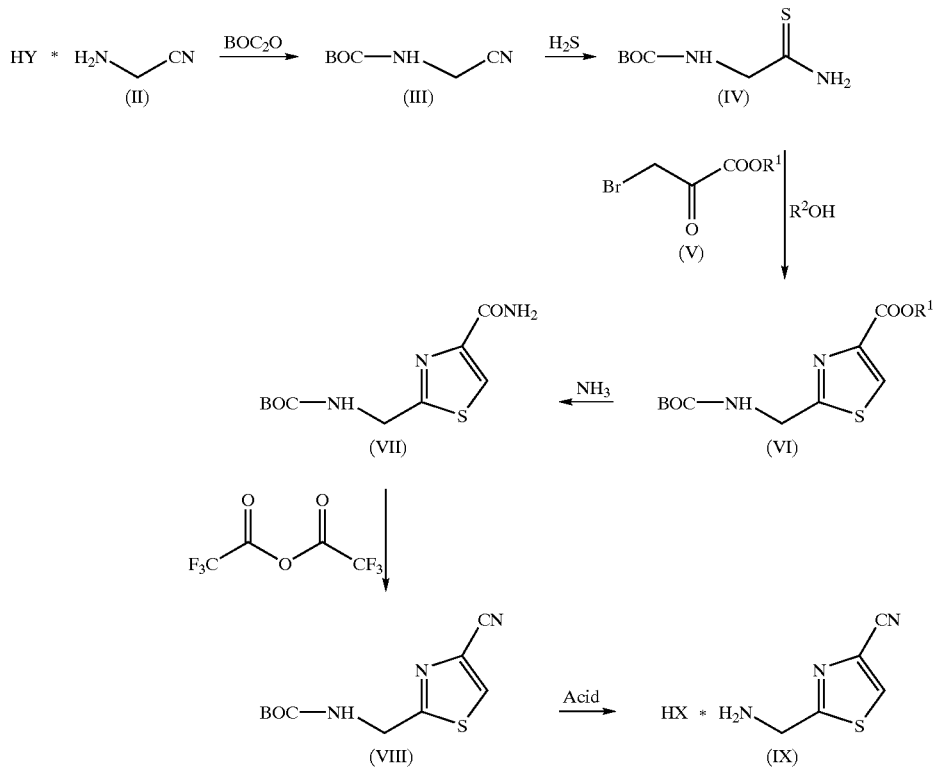

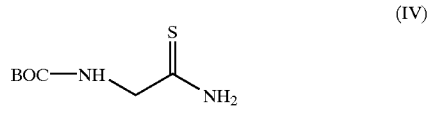

(IV)

is stirred with a bromopyruvate of the formula V,

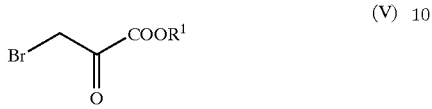

(V)

in which $R^1$ is branched or linear $C_{1-4}$-alkyl in an alcohol $R^2OH$ in which $R^2$ is branched or linear $C_{1-8}$-alkyl, HO—$CH_2$—$CH_2$—, HO—$CH_2$—$CH_2$—$CH_2$— or $C_{1-4}$-alky-O—$CH_2$—$CH_2$— at from 5° C. to 40° C. until the conversion of the thioamide IV is essentially complete.

Moreover, according to the invention the resulting thiazole carboxylic ester of the formula VI,

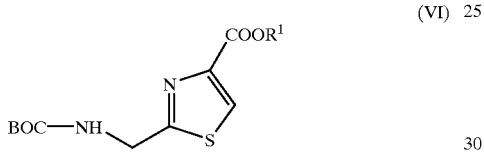

(VI)

in which $R^1$ is branched or linear $C_{1-4}$-alkyl can be stirred in an alcohol $R^2OH$ at from 0° C. to 40° C. with from 5 to 50 molar equivalents $NH_3$ of an aqueous ammonia solution until the reaction has essentially gone to completion.

The process according to the above steps can be carried out without isolating the intermediate VI.

The thiazole carboxamide of the formula VII

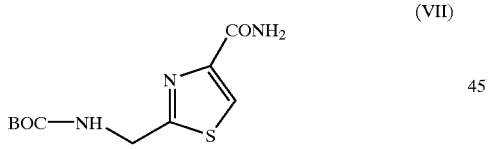

(VII)

can be filtered off as a solid.

Furthermore, the amide VII can subsequently be dehydrated to the BOC-protected 4-cyanothiazole of the formula VIII

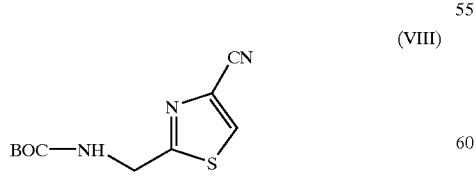

(VIII)

and the BOC protective group can be removed.

Furthermore, the invention relates to a process for preparing the compound of the formula VI

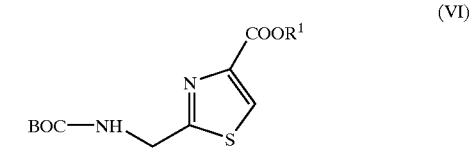

(VI)

where the thioamide of the formula IV

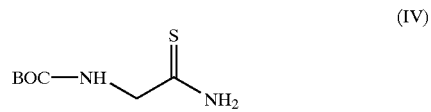

(IV)

is stirred with a bromopyruvate of the formula V,

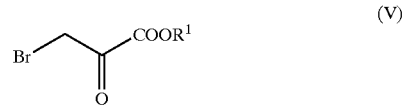

(V)

in which $R^1$ is branched or linear $C_{1-4}$-alkyl in an alcohol $R^2OH$ in which $R^2$ is branched or linear $C_{1-8}$-alkyl, HO—$CH_2$—$CH_2$—, HO—$CH_2$—$CH_2$—$CH_2$— or $C_{1-4}$-alky-O—$CH_2$—$CH_2$— at from 5° C. to 40° C. until the conversion of the thioamide IV has essentially gone to completion.

If appropriate, in the preparation of the compound of the formula VII

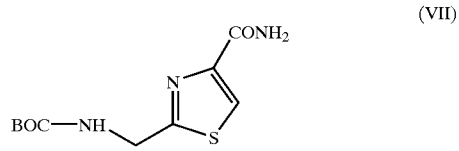

(VII)

according to the above process, the resulting thiazole carboxylic ester of the formula VI,

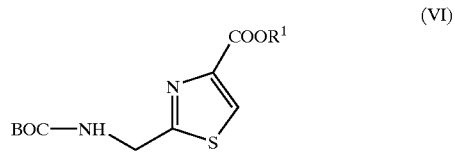

(VI)

in which $R^1$ is branched or linear $C_{1-4}$-alkyl is stirred in an alcohol $R^2OH$ at from 0° C. to 40° C. with from 5 to 50 molar equivalents $NH_3$ of an aqueous ammonia solution until the conversion has essentially gone to completion.

Alternatively, the preparation of a compound of the formula VI

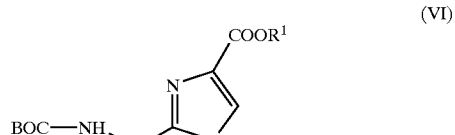

(VI)

is carried out by adding, after the conversion of the thioamide of the formula IV

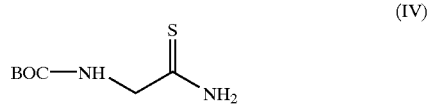

(IV)

from 0.9 to 3 molar equivalents of a base, for example an amine, an alkali metal carbonate, alkali metal bicarbonate or alkali metal hydroxide, dissolved in water or undissolved, to the solvent and, after addition of water, if appropriate distilling off the solvent $R^2OH$ to the point where the ester VI begins to precipitate out, and bringing the precipitation, if appropriate, to completion by cooling the mixture and adding more water, and filtering off the thiazole carboxylic ester.

Furthermore, the reaction of the thioamide of the formula IV

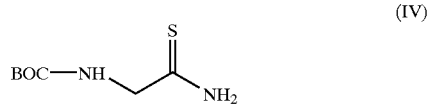

(IV)

with the bromopyruvate of the formula V

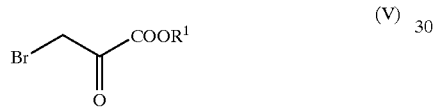

(V)

can be carried out in the solvent $R^2OH$ in which $R^2$ is preferably $C_{2-5}$-alkyl in the presence of from 1 to 3 molar equivalents of solid alkali metal bicarbonate, followed by work-up as described above.

Moreover, the process can be carried out by adding, in the preparation of a compound of the formula VII,

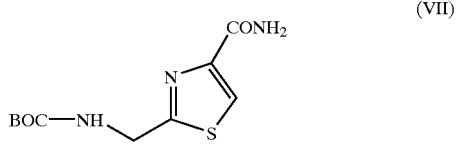

(VII)

after the conversion of the thioamide of the formula IV

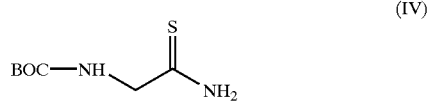

(IV)

from 1 to 5 molar equivalents $NH_3$ in the form of an aqueous ammonia solution to the solvent, distilling off from 30% to 60% of the alcohol $R^2OH$ in which $R^2$ is preferably $C_{1-5}$-alkyl, adding a further 5 to 50 molar equivalents $NH_3$ in the form of aqueous ammonia and filtering off the resulting thiazole carboxamide precipitate, if appropriate after cooling the mixture.

Furthermore, the invention relates to compounds of the formulae Ia and Ib

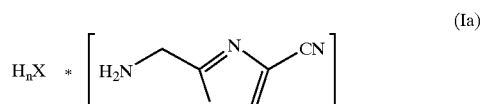

(Ia)

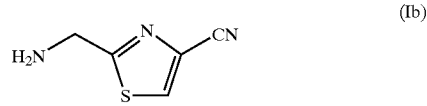

(Ib)

in which
n=1 or 2 and,
for n=1, X is chloride, bromide, triflate and hydrogen sulfate and,
for n=2, X is sulfate,
and to a compounds of the formula X

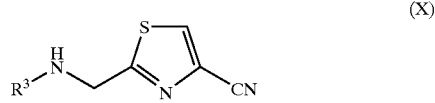

(X)

in which $R^3$ is a benzyloxycarbonyl, 9-fluorenylmethoxycarbonyl, trifluoromethylacetyl, acetyl or benzoyl radical.

Preparation of the intermediates and the end product:

EXAMPLE 1

Preparation of 2-Aminomethyl-4-cyanothiazole Hydrochloride and 2-(N-tert-Butyloxycarbonylaminomethyl)-4-cyanothiazole a) Boc-2-Aminomethylthiazole-4-carboxamide At 10° C., ethyl bromopyruvate (386 g, 1.98 mol) was added dropwise to a solution of Boc-glycinethioamide (370 g, 1.94 mol) in 3.9 liters of ethanol, and the mixture was then stirred at 20–25° C. for 5 h, after which 299 ml of a 25% strength aqueous ammonia solution were added.

From 940 ml of this mixture (corresponds to 19.9% of the total volume), 380 ml of ethanol were distilled off, a further 908 ml of a 25% strength aqueous ammonia solution were added and the mixture was stirred at 20–25° C. for 110 h. The mixture was cooled to 0° C. and the solid was filtered off, washed twice with water and dried. This gave 60.1 g of the BOC-protected thiazole carboxamide of an HPLC purity of 97.9 area %, which corresponded to a yield over these two steps of 60.5%.

$^1$H-NMR (DMSO-d$^6$, in ppm): 8.16 (s, 1H, Ar—H), 7.86 (t, broad, 1H, NH), 7.71 and 7.59 (2×s, broad, 1H each, NH$_2$), 4.42 (d, 2H, CH$_2$), 1.41 (s, 9H, tert-butyl).

b) 2-Aminomethyl-4-cyanothiazole Hydrochloride

Boc-2-aminomethylthiazole-4-carboxamide (75.0 g, 0.29 mol) was suspended in 524 ml of methylene chloride and, at from −5 to 0° C., admixed with triethylamine (78.9 g, 0.78 mol) and 79.5 g (0.38 mol) of trifluoroacetic anhydride. The mixture was stirred for another 1 h and then allowed to warm to 20–25° C., 1190 ml of water were added and the phases were separated. 160 ml of 5–6 N isopropanolic hydrochloric acid were added to the organic phase, the mixture was heated to the boil for 3 h, stirred at 20–25° C. overnight and cooled to from −5 to 0° C. for 2.5 h, and the solid was filtered off, washed with methylene chloride and dried. This gave 48.1 g of 2-aminomethyl-4-cyanothiazole of an HPLC purity of 99.4 area %, which corresponds to a yield over these two steps of 94.3%.

$^1$H-NMR (DMSO-d$^6$, in ppm): 8.98 (s, broad, 2H, NH$_2$), 8.95 (s, 1H, Ar—H), 4.50 (s, 2H, CH$_2$).

EXAMPLE 2

Preparation of 2-(N-tert-Butyloxycarbonylaminomethyl)-4-cyanothiazole

From another synthesis batch, the BOC-protected 2-aminomethyl-4-cyanothiazole was isolated in almost quantitative yield in accordance with the synthesis procedure described above.

$^1$H-NMR (DMSO-d$^6$, in ppm): 8.75 (s, Ar—H), 7.90 (t, broad, NH), 4.42 (d, CH$_2$), 1.40 (s, tert-butyl).

EXAMPLE 3

Preparation of 2-(N-tert-Butyloxycarbonylaminomethyl)-4-ethoxycarbonylthiazole

Method A:

At 20–25° C., 24.6 mmol of ethyl bromopyruvate were added to 5.0 g (24.2 mmol) of thioamide in 47 ml of isopropanol, and the mixture was stirred for 5 h. 24.0 mmol of NaOH as a 20% strength aqueous solution of sodium hydroxide were then added, the product was extracted with methyl tert-butyl ether, the organic phase was washed with water and saturated sodium chloride solution and dried over sodium sulfate and the solvent was completely stripped off. This gave 6.2 g of the ethyl thiazole carboxylate, corresponding to a yield of 89.6%.

$^1$H-NMR (DMSO-d$^6$, in ppm): 8.41 (s, 1H, Ar—H), 7.86 (t, broad, NH), 4.41 (d, 2H, CH$_2$), 4.30 (q, 2H, CH$_2$), 1.40 (s, 9H, tert-butyl), 1.30 (t, 3H, CH$_3$).

Method B:

At 20–25° C., 1.07 mol of ethyl bromopyruvate were added to 200 g (1.05 mol) of thioamide in 2.0 l of ethanol and 105 g of KHCO$_3$ powder, and the mixture was stirred overnight. 225 ml of water and 50 g of 20% strength aqueous sodium hydroxide solution were then added, about 600 ml of ethanol were distilled off, 500 ml of water were added and the mixture was cooled to 0° C. The precipitated solid was filtered off and dried. This gave 246 g of ethyl thiazole carboxylate which, according to NMR, was pure. This corresponds to a yield of 81.7%.

EXAMPLE 4

Preparation of 2-(N-Benzyloxycarbonylaminomethyl)-4-cyanothiazole

At from –5–0° C., 101 g of triethylamine and 103 g of trifluoroacetic anhydride were added to 110 g (0.38 mol) of Z-protected (Z=benzyloxycarbonyl) 2-aminomethyl-4-aminocarbonylthiazole. The mixture was stirred for 1 h and then warmed to 20–25° C. and stirred overnight. The organic phase was extracted twice with 1760 ml of water and dried over sodium sulfate, and the solvent was completely stripped off. This gave 102.9 g of the product with a purity of about 95%, corresponding to a yield of about 94%.

$^1$H-NMR (DMSO-d6, in ppm): 8.77 (s, 1H, Ar—H), 8.32 (t, broad, NH), 7.43–7.20 (m, 5H, Ar—H), 5.10 (s, 2H, OCH$_2$), 4.52 (d, 2H, CH$_2$).

EXAMPLE 5

Preparation of N-(Ethoxycarbonyl-methylene)-(D)-cyclohexylalanyl-3,4-dehydroprolyl-[2-(4-hydroxyamidino)-thiazole]methylamide Hydrochloride The 2-aminomethyl-4-cyanothiazole hydrochloride obtained under b) in Example 1 is further processed as follows:

c) 3,4-Dehydroprolyl-[2-(4-cyano)-thiazolemethyl]amide Hydrochloride

2-Aminomethyl-4-cyanothiazole hydrochloride (64 g, 364 mmol) was added to a solution of Boc-3,4-dehydroproline (77.5 g, 349 mmol) in methylene chloride (150 ml). With stirring and at from 0 to 10° C., diisopropylethylamine (157 g, 1.2 mol) was added dropwise to the suspension. At from –2 to –5° C., propanephosphonic anhydride (50% strength in ethyl acetate, 290 g, 456 mmol) was then added dropwise over a period of 2 h. After 13 h, the mixture was warmed to 20° C., and 240 ml of methylene chloride and then 310 ml of water were added. The organic phase was separated off, the aqueous phase was washed with 200 ml of methylene chloride and the organic phases were combined. The combined organic phases were admixed with 200 ml of water, and the pH was adjusted to 3 using conc. hydrochloric acid. The organic phase was once more separated off and then washed with 200 ml of water. The solvent from the organic phase was distilled off and the residue was taken up in 860 ml of isopropanol. 140 ml (about 2 molar equivalents) of isopropanolic hydrochloric acid were added, and the mixture was heated to 40–45° C. After about 12 hours, the protective group had been removed completely (TLC control). Another 140 ml of isopropanol were added, and the solution was heated at 80° C. for one hour. The solution was then slowly cooled to 0° C. and stirred at 0° C. for 18 hours, during which the title compound precipitated out as a salt. The product was filtered off and the crystals were washed with precooled isopropanol and then with diisopropyl ether. 680 g (yield 72%) of the title compound were isolated as a white crystalline product.

d) N-(tert-Butoxycarbonyl-methylene)-(Boc)-(D)-cyclohexylalanyl-3,4-dehydroprolyl-[2-(4-cyano)-thiazole]methylamide 3,4-Dehydroprolyl-[2-(4-cyano)-thiazolemethyl]amide hydrochloride (59 g, 218 mmol) were added to a solution of N-(tert-butoxycarbonyl-methylene)-(Boc)-(D)-cyclohexylalanine (preparation described in WO 9806741; 79 g, 206 mmol) in methylene chloride (640 ml). At 0–10° C., diisopropylethylamine (112 g, 867 mmol) and propane-phosphonic anhydride solution (50% strength in ethyl acetate, 193 g, 303 mmol) were added dropwise one after the other. The reaction was monitored by TLC. After the reaction had ended, the solution was warmed to room temperature, and 180 ml of water were added. The pH of the mixture was adjusted to pH 3 using conc. hydrochloric acid. The organic phase was separated off and the aqueous phase was extracted once more with 120 ml of methylene chloride. The combined organic phases were washed with another 170 ml of water at pH 3 and then with 170 ml of water and dried over magnesium sulfate, and the solvent was distilled off under reduced pressure. This gave 117 g (90% yield) of the title compound as a colorless solid substance.

e) N-(tert-Butoxycarbonyl-methylene)-(Boc)-(D)-cyclohexylalanyl-3,4-dehydroprolyl-[2-(4-hydroxyamidino)-thiazole]methylamide N-(tert-Butoxycarbonyl-methylene)-(Boc)-(D)-cyclohexylalanyl-3,4-dehydroprolyl-[2-(4-cyano)-thiazole]methylamide (22.2 g, 36.7 mmol) was dissolved in ethanol (250 ml) and admixed with hydroxyamine hydrochloride (6.41 g, 92.2 mmol), and diisopropylethylamine (23.8 g, 31.6 ml, 184.5 mmol) was slowly added dropwise with cooling (water bath) to this suspension. After 3 h of stirring at room temperature, the reaction solution was concentrated under reduced pressure using a rotary evaporator, the residue was taken up in methylene chloride/water and the aqueous phase was adjusted to pH 3 using 2N hydrochloric acid and extracted. The organic phase was washed repeatedly with water, dried over magnesium sulfate and concentrated under reduced pressure using a rotary evaporator. The residue was saturated with n-hexane, giving 22.5 g of the title compound as an almost pure white solid.

f) N-(Ethoxycarbonyl-methylene)-(D)-cyclohexylalanyl-3,4-dehydroprolyl-[2-(4-hydroxyamidino)-thiazole]methylamide Hydrochloride N-(tert-Butoxycarbonyl-methylene)-(Boc)-(D)-cyclohexylalanyl-3,4-dehydroprolyl-[2-(4-hydroxyamidino)thiazole]methylamide (2.0 g, 3.15 mmol) was dissolved in ethanol (25 ml) and admixed with 10 ml of 5N hydrochloric acid in ether, and the mixture was stirred at 60° C. for 3 h.

Since according to TLC (methylene chloride/methanol/acetic acid: 100/20/5), the conversion was still not complete, another 10 ml of 5N hydrochloric acid in ether were added and the mixture was once more stirred at 60° C. for 3 h. The reaction mixture was concentrated under reduced pressure using a rotary evaporator, and the residue was then repeatedly codistilled with ethanol and ether to remove adhering hydrochloric acid. The product was subsequently dissolved in a little methylene chloride and precipitated out with ether, and the residue was filtered off with suction and dried under reduced pressure. This gave 1.65 g of the title compound as a white hygroscopic solid substance. FAB-MS (M+H$^+$): 507

I claim:

1. A process for preparing 2-aminomethyl-4-cyanothiazole and its salts of the formulae 1a and 1b

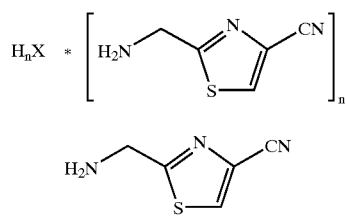

in which
n=1 or 2 and,
for n=1, X is chloride, bromide, triflate or hydrogen sulfate and
for n=2, X is sulfate, comprising a) reacting a thioamide of the formula IV

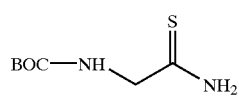

with a bromopyruvate of the formula V,

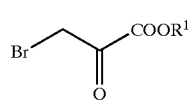

in which R$^1$ is branched or linear C$_{1-4}$-alkyl in an alcohol R$^2$OH in which R$^2$ is branched or linear C$_{1-8}$-alkyl, HO—CH$_2$—CH$_2$—, HO—CH$_2$—CH$_2$—CH$_2$— or C$_{1-4}$-alkyl-O—CH$_2$—CH$_2$— at from −5° C. to 40° C. to produce a thiazole carboxylic ester of the formula VI,

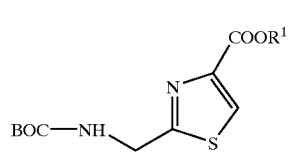

in which R$^1$ is branched or linear C$_{1-4}$ alkyl; b) reacting the thiazole carboxylic ester of formula VI in an alcohol R$^2$PH at from 0° C. to 40° C. with from 5 to 50 molar equivalents NH$_3$ of an aqueous ammonia solution where R$^2$ is as described above to produce a thiazole carboxamide of the formula VII

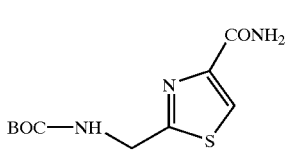

c) dehydrating the amide VII to form BOC-protected 4-cyanothiazole of the formula VIII

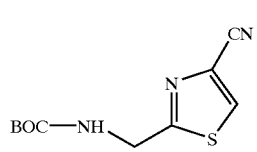

and d) removing the BOC protective group.

2. A process as claimed in claim 1, where the process steps are carried out without isolating the thiazole carboxylic ester.

3. A process for preparing a compound of the formula VI

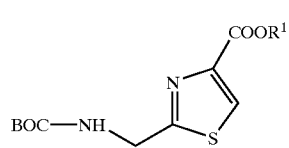

in which R$^1$ is branched or linear C$_{1-4}$ alkyl where the thioamide of the formula IV where the thioamide of the formula IV

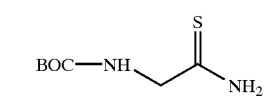

is reacted with a bromopyruvate of the formula V,

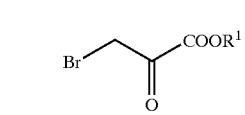

in an alcohol R$^2$OH in which R$^2$ is branched or linear C$_{1-8}$-alkyl, HO—CH$_2$—CH$_2$—, HO—CH$_2$—CH$_2$—CH$_2$— or C$_{1-4}$-alkyl-O—CH$_2$—CH$_2$— at from −5° C. to 40° C.

4. A process as claimed in claim 3 where the compound of the formula VI,

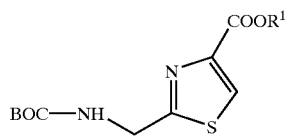

in which $R^1$ is branched or linear $C_{1-4}$-alkyl is reacted in an alcohol $R^2OH$ at from 0° C. to 40° C. with from 5 to 50 molar equivalents $NH_3$ of an aqueous ammonia solution to produce a compound of the formula VII

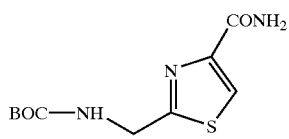

5. A process according to claim 1, where, in the preparation of a compound of the formula VI

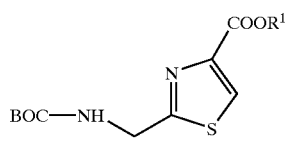

after the conversion of the thioamide of the formula IV

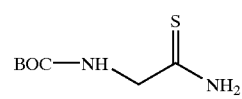

from 0.9 to 3 molar equivalents of a base, dissolved in water or undissolved, are added to the solvent and, after addition of water, if appropriate the solvent $R^2OH$ is distilled off to the point where the ester VI begins to precipitate out, and the precipitation is, if appropriate, brought to completion by cooling the mixture and adding more water, and the thiazole carboxylic ester is filtered off.

6. A process as claimed in claim 1, where the reaction of the thioamide of the formula IV

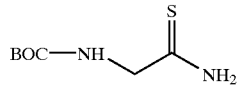

with the bromopyruvate of the formula V

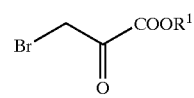

is carried out in the solvent $R^2OH$ in which $R^2$ is $C_{2-5}$-alkyl in the presence of from 1 to 3 molar equivalents of solid alkali metal bicarbonate.

7. A process as claimed in claim 1, where, in the preparation of a compound of the formula VII

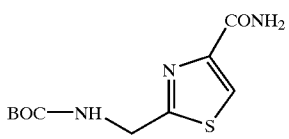

after the conversion of the thioamide of the formula IV

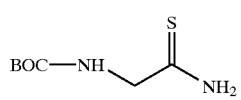

from 1 to 5 molar equivalents $NH_3$ are added to the solvent in the form of an aqueous ammnonia solution, from 30% to 60% of the alcohol $R^2OH$ in which $R^2$ is preferably $C_{1-5}$-alkyl are distilled off, a further 5 to 50 molar equivalents $NH_3$ are added in the form of aqueous ammonia and the resulting thiazole carboxamide precipitate is filtered off, if appropriate after cooling the mixture.

8. A compound of the formula X

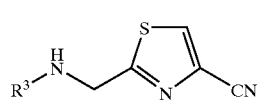

in which $R^3$ is a benzyloxycarbonyl, 9-fluorenylmethoxycarbonyl, trifluoromethylacetyl, acetyl or benzoyl radical.

* * * * *

UNITED STATES PATENT AND TRADEMARK OFFICE
CERTIFICATE OF CORRECTION

PATENT NO. : 6,642,388 B1
DATED : November 4, 2003
INVENTOR(S) : Thomas Pfeiffer It is certified that error appears in the above-identified patent and that said Letters Patent is hereby corrected as shown below:

<u>Title page,</u>
Item [73], Assignee, change "Munich" to -- "Wiesbaden --.

Signed and Sealed this

Sixteenth Day of March, 2004

JON W. DUDAS
*Acting Director of the United States Patent and Trademark Office*